(12) United States Patent
Kai et al.

(10) Patent No.: US 6,407,070 B1
(45) Date of Patent: Jun. 18, 2002

(54) SOLID PHARMACEUTICAL COMPOSITION FOR DIALYSATE CONTAINING SODIUM BICARBONATE AND A PROCESS FOR PRODUCING THE SAME

(75) Inventors: Toshiya Kai; Kazuyuki Yamamoto; Kazutaka Fujiki; Hiroaki Kato; Makoto Sato, all of Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/655,450

(22) Filed: Sep. 5, 2000

(30) Foreign Application Priority Data

Sep. 7, 1999 (JP) ............................................ 11-252671

(51) Int. Cl.$^7$ ........................ A61K 33/00; A61K 9/00; A61K 9/14
(52) U.S. Cl. ........................ 514/23; 424/400; 424/490; 514/23; 514/784
(58) Field of Search ................... 514/23, 784; 424/600, 424/400, 490

(56) References Cited

U.S. PATENT DOCUMENTS 4,889,634 A  * 12/1989  El-Rashidy ................. 210/646
5,540,842 A  *  7/1996  Aoyama et al. ............ 210/647

FOREIGN PATENT DOCUMENTS

| JP | 2-311418 A | 12/1990 |
| JP | 3-38527 A | 2/1991 |
| JP | 03066621 | * 3/1991 |
| JP | 03066622 | * 3/1991 |
| JP | 5-70357 A | 3/1993 |
| JP | 7-24061 A | 1/1995 |
| JP | 7-59846 A | 3/1995 |
| JP | 8-92070 A | 4/1996 |
| WO | WO 2001078804 | * 10/2001 |

OTHER PUBLICATIONS

Ahmad et al. "Dialysate made from dry chemicals using citric acid increases dialysis dose." Am. J. Kidney Dis. (2000), 35(3), 493–499 (abstract).*

* cited by examiner

Primary Examiner—Ralph Gitomer
Assistant Examiner—Devesh Khare
(74) Attorney, Agent, or Firm—Kubovcik & Kubovcik

(57) ABSTRACT

A one-pack solid pharmaceutical composition for dialysate containing sodium bicarbonate which can prevent the reactions between sodium bicarbonate and acetic acid and between sodium bicarbonate and electrolytes, and is excellent in long term storage stability is provided. The solid pharmaceutical composition for dialysate containing sodium bicarbonate is a mixture of an agent A containing sodium chloride, calcium chloride, magnesium chloride, potassium chloride, sodium acetate and acetic acid and an agent B containing sodium bicarbonate coated with sodium acetate.

6 Claims, No Drawings

SOLID PHARMACEUTICAL COMPOSITION FOR DIALYSATE CONTAINING SODIUM BICARBONATE AND A PROCESS FOR PRODUCING THE SAME

FIELD OF THE INVENTION

The present invention relates to a solid pharmaceutical composition for preparing a dialysate containing sodium bicarbonate and a process for producing the same.

BACKGROUND OF THE INVENTION

When blood dialysis is performed on patients suffering from decreased kidney function, the blood of the patient is cleaned in an artificial kidney. In the inside of the artificial kidney, generally, a dialysate is perfused to allow waste materials in the blood to be transferred through a dialysis membrane to the dialysate. As the dialysate, acetic acid-containing dialysate has been used. Recently, the acetic acid-containing dialysate has come to be increasingly replaced by those in which sodium bicarbonate, which alleviates unpleasant symptoms during the dialysis, is used.

The dialysate which contains sodium bicarbonate usually is prepared from two kinds of dialysis preparation, one being a preparation containing electrolyte components other than sodium bicarbonate (for example, sodium chloride, potassium chloride, calcium chloride, magnesium chloride, sodium acetate) and a pH adjusting agent (for example, acetic acid) (hereinafter, referred to as agent A) and the other being a preparation containing sodium bicarbonate (hereinafter, referred to as agent B). The dialysate preparations may sometimes contain sugars such as glucose or may be mixed with another preparation containing a sugar.

Conventionally, agents A and B have been available in the state of concentrated solutions adjusted to predetermined concentrations. However, since about 300 L of dialysate is required for one dialysis operation for a single patient, large amounts of concentrated solutions are used and diluted with water when many patients are subjected to dialysis therapy in a medical ward. Accordingly, to reduce the loads imposed on persons who prepare dialysate and to save space, agent B in the form of a powdered preparation has been increasingly used. In accordance therewith, a solid pharmaceutical preparation for dialysate containing sodium bicarbonate that is composed of two agents including agent A in the form of a powder has been developed. Furthermore, a solid pharmaceutical preparation for dialysate containing sodium bicarbonate as a "one-pack" has been reported but no commercial product has been put on the market.

As solid pharmaceutical preparations for dialysate containing sodium bicarbonate there have been disclosed dialysis compositions composed of two preparations, one being powdery agent A composed of electrolytes (other than sodium bicarbonate), glucose and liquid acid and the other being powdery agent B composed of sodium bicarbonate alone or of sodium bicarbonate and sodium acetate or glucose (Japanese Patent No. 2749375, Japanese Patent No. 2751933, and JP-A-3-38527). However, these dialysis compositions are such that the agents A and B are separately stored and, immediately before use, are dissolved into water and mixed together and then used for the blood dialysis. When the agent A and agent B are mixed in advance, the sodium bicarbonate contained in the agent B and the calcium salt and magnesium salt contained in the agent A react due to the crystal water contained in the salts or moisture in the air to form sparingly soluble salts. Also, the sodium bicarbonate contained in the agent B and the acetic acid contained in the agent A react with each other to generate carbon dioxide gas so that the pH of the dialysate after it is dissolved in a predetermined amount of water cannot be maintained in an appropriate range.

As a one-pack dialysis preparation developed taking the above defects into consideration, a mixture of a granulated product consisting of electrolytes including a calcium component but not sodium bicarbonate and another granulated product consisting of eletrolytes including sodium bicarbonate but not a calcium component is disclosed (JP-A-3-74331). Also, a granulated dialysis composition is disclosed which comprises separate granulated compositions, one being composed of electrolytes other than sodium bicarbonate and a acid and the other being composed of glucose and sodium bicarbonate (JP-A-5-70357, Japanese Patent No. 2809971). Further, a dialysis composition which comprises a powdery preparation containing electrolytes (other than sodium bicarbonate) and acetic acid, and a powdery preparation containing sodium bicarbonate in which the acetic acid is contained as sodium diacetate (JP-A-7-59846) are disclosed. However, these dialysis compositions have been prepared merely by granulating substances that are reactive separately from each other and then mixing. Therefore, it is difficult to prevent production of salts or generation of carbon dioxide gas after the mixing. Since the dialysis compositions are prepared by a wet granulation method, there is the fear that sodium bicarbonate will be colored due to the heat during a drying step or coloring and decomposition of glucose will occur. Furthermore, if the dialysis composition is prepared by use of sodium diacetate in which acetic acid is adsorbed with sodium acetate, it is difficult to have the total amount of acetic acid adsorbed completely so that there is the possibility that the non-adsorbed acetic acid will react with sodium bicarbonate.

On the other hand, there has been disclosed a mixture of a dialysis preparation composed of a first agent containing electrolytes (other than sodium bicarbonate) and acid, and a second agent containing sodium bicarbonate and remaining electrolytes not used in the first agent (JP-A-8-92070). The first agent and/or the second agent are covered with a coating layer composed of at least one substance selected from the group consisting of sodium chloride, potassium chloride and glucose, and citric acid is used as the acid in the embodiment of this patent application. The dialysis preparation is free of the fear that sparingly soluble salts will be produced since the coating layer prevents the reaction of sodium bicarbonate with calcium salt and magnesium salt.

However, when the acid contained in the first agent is acetic acid, the covering layer alone cannot prevent a reaction between the acetic acid contained in the first agent and the sodium bicarbonate contained in the second agent after the mixing of the first and second agents. If the first agent contains sodium acetate as an electrolyte and when the sodium acetate adsorbs acetic acid, there is a fear that the non-adsorbed acetic acid will react with the sodium bicarbonate contained in the second agent. Also, when the sodium acetate is contained in the second agent but is not contained in the first agent, it is difficult to stop evaporation of acetic acid during the process of preparing the first agent. Even if the first agent could be produced, there is the possibility that acetic acid will react with sodium bicarbonate before it is adsorbed by sodium acetate since the second agent is a simple mixture of sodium acetate and sodium bicarbonate. Furthermore, since the dialysis composition is prepared by a wet granulation method, there is the possibility that coloring of sodium bicarbonate and coloring and decomposition of glucose will occur.

SUMMARY OF THE INVENTION

Under the above circumstances, an object of the present invention is to provide a one-pack solid pharmaceutical composition for dialysate containing sodium bicarbonate without reaction between sodium bicarbonate and acetic acid and without reaction between sodium bicarbonate and electrolytes such as calcium chloride or magnesium chloride, and which is excellent in long term storage stability.

The present inventors have made extensive research with a view to solving the above problems. And as a result, they found that the above object can be attained by adding sodium acetate to both of agent A containing electrolytes (other than sodium bicarbonate) and acetic acid and agent B containing sodium bicarbonate, and furthermore coating the sodium bicarbonate contained in the agent B with the sodium acetate, thus completing the present invention.

That is, the present invention provides a solid pharmaceutical composition for dialysate containing sodium bicarbonate (hereinafter at times called a solid sodium bicarbonate dialysis preparation) comprising a mixture of an agent A containing sodium chloride, calcium chloride, magnesium chloride, potassium chloride, sodium acetate and acetic acid, and an agent B containing sodium bicarbonate coated with sodium acetate.

Also, the present invention provides a method for producing a solid sodium bicarbonate dialysis preparation comprising the following steps (1) to (4):

(1) spraying an aqueous solution containing calcium chloride, magnesium chloride, potassium chloride and sodium acetate onto core particles which are composed essentially of sodium chloride, and drying them, (2) mixing the product obtained in step (1) with acetic acid to obtain an agent A, (3) spraying an aqueous solution containing sodium acetate onto core particles of sodium bicarbonate and drying them to obtain an agent B, and (4) mixing the agent A obtained in the step (2) with the agent B obtained in step (3).

In the present invention, as the sodium chloride core particles contained in the agent A, a crystalline one having a particle diameter of about 75 to 1,700 μm is preferably used.

As the calcium chloride contained in the agent A in the present invention, calcium chloride dihydrate, calcium chloride monohydrate, anhydrous calcium chloride, etc. are preferably used and as the magnesium chloride, magnesium chloride hexahydrate, etc. are preferably used.

As the acetic acid contained in the agent A in the present invention, glacial acetic acid, acetic anhydride, etc. are used preferably.

In the present invention, anhydrous sodium acetate, sodium acetate trihydrate, etc. are used preferably as the sodium acetate contained in the agents A and B.

The agent A in the present invention may contain glucose, if necessary. As the glucose used in the present invention, a glucose powder having a particle diameter of about 45 to 1,700 μm is preferred.

In the present invention, the sodium bicarbonate core particles contained in the agent B may be either powder or granules, and one comprising granules having a particle diameter of 75 to 1,700 μm, preferably 355 to 1,700 μm, is preferred.

In the present invention, the solid sodium bicarbonate dialysis preparation is dissolved in water to prepare a dialysate. The dialysate has the following composition (final concentration), for example:

| | |
|---|---|
| $Na^+$ | 120 to 150 mEq/L |
| $K^+$ | 0.5 to 3 mEq/L |
| $Ca^{2+}$ | 1.5 to 4.5 mEq/L |
| $Mg^{2+}$ | 0.1 to 2.0 mEq/L |
| $Cl^-$ | 90 to 135 mEq/L |
| $CH_3COO^-$ | 5 to 15 mEq/L |
| $HCO_3^-$ | 20 to 35 mEq/L |
| Glucose | 0 to 2.5 g/L. |

In the present invention, the agent A is of a structure comprising core particles composed essentially of sodium chloride, with the core particles being covered with a coating layer composed of calcium chloride, magnesium chloride, potassium chloride, sodium acetate and acetic acid.

The core particles which are composed essentially of sodium chloride may contain a small amount of magnesium chloride, calcium chloride, potassium chloride, sodium acetate, etc., in addition to sodium chloride. It is sometimes the case that the acetic acid contained in the coating layer penetrates into the inside of the core particles but usually there is no fear that this will change the properties of the dialysis preparation. Upon preparing the agent A of the present invention, each component of the core particles may be used as it is without pulverization, or may be pulverized in advance into a granular state of a particle diameter of 75 to 1,700 μm by use of a pulverizer or a particle size selector. Otherwise, it may be granulated into granules of a similar size by a wet or dry granulation method.

The compounds contained in the coating layer may contain sodium chloride in addition to the above components. The compounds are dissolved in water to prepare an aqueous solution, which is then coated onto the granules.

The agent A in the present invention may contain glucose. The glucose is optionally mixed in the form of a powder during the step of coating an aqueous solution of the compounds contained in the coating layer onto the core particles. Preferably, the glucose is previously pulverized to granules having a particle diameter of 45 to 1,700 μm by use of a pulverizer.

The agent B in the present invention is sodium bicarbonate coated with sodium acetate.

Upon producing the agent B of the present invention, the sodium bicarbonate may be used as it is without pulverization but one previously granulated into granules of a particle diameter of 75 to 1,700 μm, preferably 355 to 1,700 μm, is used. The sodium acetate is dissolved in water to prepare an aqueous solution, which is then coated onto the sodium bicarbonate.

The agent A in the present invention can be obtained by granulation according to a centrifugal fluidized bed granulation method, a fluidized bed granulation method, an agitating fluidized bed granulation method, or the like. Preferably, an agitating fluidized bed granulation method is used. The agent B in the present invention can be obtained by a dry compressed granulation method, an extrusion granulation method, or the like. Preferably, a dry compressed granulation method requiring no drying step is used.

Hereinafter, the production of the solid composition for dialysis of the present invention will be described.

(1) First, 1,500 g of sodium chloride for forming core particles is charged into, for example, an agitating fluidized bed granulator. Onto the core particles is sprayed an aqueous solution containing 27 to 81 g of calcium chloride, 2.5 to 49.8 g of magnesium chloride, 9 to 54 g of potassium chloride and 70 to 202 g of sodium acetate followed by drying to form a coating layer. The concentration of the aqueous solution is preferably 15 to 50% by weight, and particularly preferably 25 to 40% by weight. If the concentration of the aqueous solution is lower than 15% by weight, a larger amount of the aqueous solution must be used so that the coating time becomes longer. On the other hand, if it is higher than 50% by weight, the compounds forming the coating layer are not dissolved completely so that there is a fear that a suspension will result.

The agitating fluidized bed granulator is used to effect rolling of the core particles by means of fluidizing action caused from air flow in the vicinity of the wall and agitation action caused from rotation by a rotater on the bottom of the granulator, and spray coating of the components in the aqueous solution onto the core particles.

The flow rate of the air flow is preferably 0.2 to 200 m$^3$/min and particularly preferably 0.5 to 100 m$^3$/min. If the flow rate is less than 0.2 m$^3$/min, the core particles tend to aggregate while if it is more than 200 m$^3$/min, the components in the aqueous solution tend to cause a spray dry phenomenon. In addition, each particle receives greater impact so that it tends to become a fine powder. The revolution of the rotor is preferably 20 to 1,000 rpm and particularly preferably 50 to 500 rpm. If the revolution is smaller than 20 rpm, the thickness of the coating layer becomes uneven while if it is greater than 1,000 rpm, there is the fear that the coating layer will be scraped off due to the mutual collision between the coated granules or friction of the coated granules with the inner wall of the granulator. It is preferred that the drying be performed continuously at an exhaust gas temperature of 25 to 70° C. during the spraying. The water content of the granulated product after the drying is preferably 0 to 10%.

In the case where the coating layer contains glucose, it is preferred that the glucose be charged into the granulator as it is in the form of a powder when a state is reached where 10 to 90% in amount of the aqueous solution has been coated on the core particles. If the amount of the aqueous solution coated on the core particles is less than 10% and the glucose has been charged in the initial stage of the coating, coloring and decomposition of glucose due to heat tend to occur. On the other hand, if it is more than 90%, there is a fear that the thickness of the coating layer will be uneven.

(2) The granulated product obtained in the step (1) is taken out from the agitating fluidized bed granulator, spontaneously cooled, and charged into a V-type mixer or the like. Then, 22 to 52 g of glacial acetic acid is added and the mixture is mixed to produce agent A. The obtained granulated product preferably has a mean particle diameter of 75 to 1,700 μm and a water content of 0 to 10%.

(3) 1,500 g of sodium bicarbonate serving as core particles is charged into the agitating fluidized bed granulator. An aqueous solution containing 10 to 320 g of sodium acetate is sprayed onto the core particles, followed by drying to form a coating layer, thus granulating agent B. The obtained granulated product has a mean particle diameter of 75 to 1,700 μm.

The concentration of the aqueous solution is preferably 10 to 50% by weight and particularly preferably 15 to 45% by weight. If it is lower than 10% by weight, the coating time becomes longer since the amount of the aqueous solution increases. And if it is higher than 50% by weight, the compounds forming the coating layer are not dissolved completely, so that there is a fear that a suspension will result. The flow rate in the agitating fluidized bed granulator and the revolution of the rotor are preferably the same as those in the step (1). It is preferred that the drying is performed continuously at an exhaust gas temperature of 20 to 70° C. during the spraying. The water content of the granulated product after drying is referably 0 to 10%.

(4) The agent A obtained in step (2) and the agent B obtained in step (3) are charged into a V-type mixer or the like such that a predetermined blending ratio will be reached and are mixed for 5 to 30 minutes to obtain a solid sodium bicarbonate dialysis preparation of the present invention. The obtained granulated product has a mean particle diameter of 75 to 1,700 μm and a water content of 0 to 10%.

EXAMPLES

Hereinafter, the present invention will be described in detail by way of examples. However, the present invention should not be limited to the examples.

(Preparation of Agent A)

[A-1]

Into an agitating fluidized bed granulator (Multiplex MP-01, manufactured by Powrex Co.) was charged 1,500 g of sodium chloride having a mean particle diameter of 300 μm as core particles. An aqueous solution of 36.6 g of potassium chloride, 25.0 g of magnesium chloride hexahydrate, 45.1 g of calcium chloride dihydrate and 80.6 g of anhydrous sodium acetate dissolved in 447.8 g of purified water was sprayed thereon at an air feed temperature of 80° C., a rotor revolution of 300 rpm, and an air feed flow rate of 40 m$^3$/hr and was simultaneously dried to coat the sodium chloride core particles therewith. After 20 minutes, when about half an amount of the aqueous solution was coated on the core particles, 245.6 g of glucose powder having a mean particle diameter of 180 μm was added into the granulator and the remaining aqueous solution was subsequently sprayed to obtain granules having a mean particle diameter of 850 μm. The granules were taken out from the granulator and cooled down to room temperature. Thereafter, the granules were charged into a V-type mixer (S-3 Model, manufactured by Tsutsui Rikagaku Kikai Co.) into which 36.9 g of glacial acetic acid was added and mixed uniformly to obtain agent A having a mean particle diameter of 850 μm.

[A-2]

Into an agitating fluidized bed granulator (Multiplex MP-01, manufactured by Powrec Co.) was charged 1,500 g of sodium chloride having a mean particle diameter of 300 μm as core particles, and an aqueous solution of 36.6 g of potassium chloride, 25.0 g of magnesium chloride hexahydrate, 45.1 g of calcium chloride dihydrate and 90.7 g of anhydrous sodium acetate dissolved in 471.8 g of purified water was sprayed thereon at an air feed temperature of 80° C., a rotor revolution of 300 rpm, and an air feed flow rate of 40 m$^3$/hr and was simultaneously dried to coat the sodium chloride core particles therewith. After 25 minutes, when about a half the amount of the aqueous solution was coated on the core particles, 245.6 g of glucose powder having a mean particle diameter of 180 μm was added into the granulator and the remaining aqueous solution was subsequently sprayed to obtain granules having a mean particle diameter of 1,000 μm. The granules were taken out from the granulator and cooled down to room temperature. Thereafter, the granules were charged into a V-type mixer (S-3 Model, manufactured by Tsutsui Rikagaku Kikai) in which 36.9 g of glacial acetic acid was added and mixed uniformly to obtain agent A having a mean particle diameter of 1,000 μm.

[A-3]

Into an agitating fluidized bed granulator (Multiplex MP-01, manufactured by Powrec Co.) was charged 1,500 g of sodium chloride having a mean particle diameter of 500 $\mu$m as core particles and an aqueous solution of 36.6 g of potassium chloride, 25.0 g of magnesium chloride hexahydrate, 45.1 g of calcium chloride dihydrate and 110.8 g of anhydrous sodium acetate dissolved in 519.9 g of purified water was partly sprayed thereon at an air feed temperature of 80° C., a rotor revolution of 300 rpm, and an air feed flow rate of 40 m$^3$/hr and was simultaneously dried to coat the sodium chloride core particles. After 28 minutes, when about half an amount of the aqueous solution was coated on the core particles, 245.6 g of glucose powder having a mean particle diameter of 180 $\mu$m was added into the granulator and the remaining aqueous solution was subsequently sprayed to obtain granules having a mean particle diameter of 1,100 $\mu$m. The granules were taken out from the granulator and cooled down to room temperature. Thereafter, the granules were charged into a V-type mixer (Model S-3, manufactured by Tsutsui Rikagaku Kikai) in which 36.9 g of glacial acetic acid was added and mixed uniformly to obtain agent A having a mean particle diameter of 1,100 $\mu$m.

(Preparation of Agent B)

[B-1]

Into a roller compactor (TF-MINI, manufactured by Freund Sangyo Co.) was charged 3,000 g of sodium bicarbonate having a mean particle diameter of 100 $\mu$m. Granules having a particle diameter of 300 to 1,700 $\mu$m were obtained by a dry granulation method. 1,500 g of the sodium bicarbonate granules was charged into an agitating fluidized bed granulator (Multiplex MP-01, manufactured by Powrex Co.) and an aqueous solution of 78.5 g of anhydrous sodium acetate dissolved in 183.2 g of purified water was sprayed thereon at an air feed temperature of 80° C., a rotor revolution of 200 rpm, and an air feed flow rate of 30 m$^3$/hr and was simultaneously dried to obtain agent B having a particle diameter of 355 to 1,700 $\mu$m.

[B-2]

Into a roller compactor (TF-MINI, manufactured by Freund Sangyo Co.) was charged 3,000 g of sodium bicarbonate having a mean particle diameter of 75 $\mu$m. Agent B having a particle diameter of 300 to 1,700 $\mu$m was obtained by a dry granulation method.

[B-3]

Into a roller compactor (TF-MINI, manufactured by Freund Sangyo Co.) was charged 3,000 g of sodium bicarbonate having a mean particle diameter of 75 $\mu$m. Granules having a particle diameter of 300 to 1,700 $\mu$m were obtained by a dry granulation method. 1,500 g of the sodium bicarbonate granules was charged into an agitating fluidized bed granulator (Multiplex MP-01, manufactured by Powrex Co.) and an aqueous solution of 60.7 g of sodium chloride dissolved in 344 g of purified water was sprayed thereon at an air feed temperature of 80° C., a rotor revolution of 200 rpm, and an air feed flow rate of 30 m$^3$/hr and was simultaneously dried to obtain agent B having a particle diameter of 355 to 1,700 $\mu$m.

[B-4]

Into a roller compactor (TF-MINI, manufactured by Freund Sangyo Co.) was charged 3,000 g of sodium bicarbonate having a mean particle diameter of 75 $\mu$m. Granules having a particle diameter of 300 to 1,700 $\mu$m were obtained by a dry granulation method. 1,500 g of the sodium bicarbonate granules was charged into an agitating fluidized bed granulator (Multiplex MP-01, manufactured by Powrex Co.) and an aqueous solution of 60.7 g of sodium chloride and 78.5 g of anhydrous sodium acetate dissolved in 493.5 g of purified water was sprayed thereon at an air feed temperature of 80° C., a rotor revolution of 200 rpm, and an air feed flow rate of 30 m$^3$/hr and was simultaneously dried to obtain agent B having a particle diameter of 355 to 1,700 $\mu$m.

[B-5]

After 10 kg of sodium bicarbonate having a mean particle diameter of 100 $\mu$m and 523.3 g of anhydrous sodium acetate having a mean particle diameter of 100 $\mu$m were uniformly mixed in a V-type mixer (Model S-3, manufactured by Tsutsui Rikagaku Kikai), the obtained mixture was charged into a roller compactor (TF-MINI, manufactured by Freund Sangyo Co.) and agent B having a particle diameter of 300 to 1,700 $\mu$m was obtained by a dry granulation method.

[B-6]

After 10 kg of sodium bicarbonate having a mean particle diameter of 100 $\mu$m, 523.3 g of anhydrous sodium acetate having a mean particle diameter of 100 $\mu$m and 404.7 g of sodium chloride having a mean particle diameter of 100 $\mu$m were uniformly mixed in a V-type mixer (Model S-3, manufactured by Tsutsui Rikagaku Kikai), the obtained mixture was charged into a roller compactor (TF-MINI, manufactured by Freund Sangyo Co.) and agent B having a particle diameter of 300 to 1,700 $\mu$m was obtained by a dry granulation method.

Example 1

842.1 g of the agent A obtained in [A-1] and 260 g of the agent B obtained in [B-1] were charged into a V-type mixer (Model S-3, manufactured by Tsutsui Rikagaku Kikai), and were uniformly mixed to prepare a solid sodium bicarbonate dialysis preparation.

Example 2

846.4 g of the agent A obtained in [A-1] and 260 g of the agent B obtained in [B-1] were charged into a V-type mixer and were uniformly mixed to prepare a solid sodium bicarbonate dialysis preparation.

Comparative Example 1

855 g of the agent A obtained in [A-3] and 247.1 g of the agent B obtained in [B-2] were charged into a V-type mixer and were uniformly mixed to prepare a solid sodium bicarbonate dialysis preparation.

Comparative Examples 2 to 5

842.1 g of the agent A obtained in [A-1] and 257.1 g, 270 g, 260 g, or 270 g of the agent B obtained in [B-3], [B-4], [B-5] or [B-6], respectively, were charged into a V-type mixer and uniformly mixed to prepare a solid pharmaceutical composition containing sodium bicarbonate.

(Stability Test)

50 g each of the solid sodium bicarbonate dialysis preparations obtained in Examples 1 and 2 and Comparative Examples 1 to 5 was wrapped by an aluminum wrapping material of 100×100 mm and stored (A) at 25° C. and 60% RH for 2 months or (B) at 40° C. and 75% RH for 1 month. The samples were observed for coloring of the solid sodium bicarbonate dialysis preparation in the bag and expansion of the bag due to generation of carbon dioxide gas. The coloring was measured using a color-difference meter (Z-300A, manufactured by Nippon Denshoku Co.) and generation of carbon dioxide was evaluated by the change in volume of the bag (water dipping method). The results are shown in Table 1.

TABLE 1

|  | Agent A | Agent B | Stability Test (A) | | Stability Test (B) | |
| --- | --- | --- | --- | --- | --- | --- |
|  |  |  | Coloring | Generation of carbon dioxide gas (mL) | Coloring | Generation of carbon dioxide gas (mL) |
| Example 1 | A-1 | B-1 | No | 0 | No | 0 |
| Example 2 | A-2 | B-1 | No | 0 | No | 0 |
| Comparative Example 1 | A-3 | B-2 | Yes | 53 | Yes | 150 |
| Comparative Example 2 | A-1 | B-3 | Yes | 54 | Yes | 136 |
| Comparative Example 3 | A-1 | B-4 | Yes | 49 | Yes | 142 |
| Comparative Example 4 | A-1 | B-5 | Yes | 55 | Yes | 155 |
| Comparative Example 5 | A-1 | B-6 | Yes | 56 | Yes | 147 |

As is apparent from Table 1, the solid sodium bicarbonate dialysis preparation of the present invention caused no coloring after long term storage and showed no expansion of the bag due to the generation of carbon dioxide gas.

Advantageous Effects of the Invention

The solid sodium bicarbonate dialysis preparation of the present invention can completely prevent the reaction between acetic acid and sodium bicarbonate when the agents A and B are mixed with each other so that a one-pack dialysis preparation excellent in long term storage stability can be obtained. Furthermore, in the present invention, there is no fear that coloring of sodium bicarbonate and coloring and decomposition of glucose due to heat will occur.

What is claimed is:

1. A solid pharmaceutical composition for preparing a dialysate containing sodium bicarbonate, said composition comprising a mixture of a granular agent A containing sodium chloride, calcium chloride, magnesium chloride, potassium chloride, sodium acetate and acetic acid and a granular agent B containing sodium bicarbonate coated with sodium acetate, wherein the ratio of the sodium acetate to sodium bicarbonate in the agent B is (10 to 320)/1,500 by weight.

2. The solid pharmaceutical composition for dialysate containing sodium bicarbonate as claimed in claim 1, wherein the agent A contains glucose.

3. The solid pharmaceutical composition for dialysate containing sodium bicarbonate as claimed in claim 1, wherein the agent A comprises core particles composed essentially of sodium chloride and a coating layer containing calcium chloride, magnesium chloride, potassium chloride, sodium acetate and acetic acid, the core particles being covered with the coating layer.

4. The solid pharmaceutical composition for dialysate containing sodium bicarbonate as claimed in claim 3, wherein the coating layer contains glucose.

5. A method for producing a solid pharmaceutical composition for preparing a dialysate containing sodium bicarbonate comprising the following steps (1) to (4):

(1) spraying an aqueous solution containing calcium chloride, magnesium chloride, potassium chloride and sodium acetate onto core particles composed essentially of sodium chloride and drying them, (2) mixing the product obtained in step (1) with acetic acid to obtain a granular agent A, (3) spraying an aqueous solution containing sodium acetate onto core particles of sodium bicarbonate and drying them to obtain a granular agent B, wherein the ratio of the sodium acetate to sodium bicarbonate in the agent B is (10 to 320)/1,500 by weight, and (4) mixing the granular agent A obtained in the step (2) with the granular agent B obtained in the step (3).

6. The method for producing a solid pharmaceutical composition for dialysate containing sodium bicarbonate as claimed in claim 5, wherein step (1) includes a step of mixing glucose therein.

* * * * *